US00PP29310P2

(12) United States Plant Patent
Danziger

(10) Patent No.: US PP29,310 P2
(45) Date of Patent: May 22, 2018

(54) ***PETUNIA* PLANT NAMED 'DAMORJOY'**

(50) Latin Name: *Petunia hybrida*
Varietal Denomination: DAMORJOY

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days. days.

(21) Appl. No.: 15/731,014

(22) Filed: Apr. 7, 2017

(51) Int. Cl.
*A01H 5/02* (2018.01)

(52) U.S. Cl.
USPC ..... Plt./356.13
CPC ..... *A01H 5/02* (2013.01)

(58) Field of Classification Search
USPC ..... Plt./356.13, 356.1
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Petunia* cultivar named 'DAMORJOY' is disclosed, characterized by a mounded growth habit combined with very good branching on plants of medium vigor. The flower color is burgundy purple with white stripes. The flowers are large and plants flower abundantly. The new variety is a *Petunia*, normally produced as an outdoor garden or container plant.

2 Drawing Sheets

Figure 1:
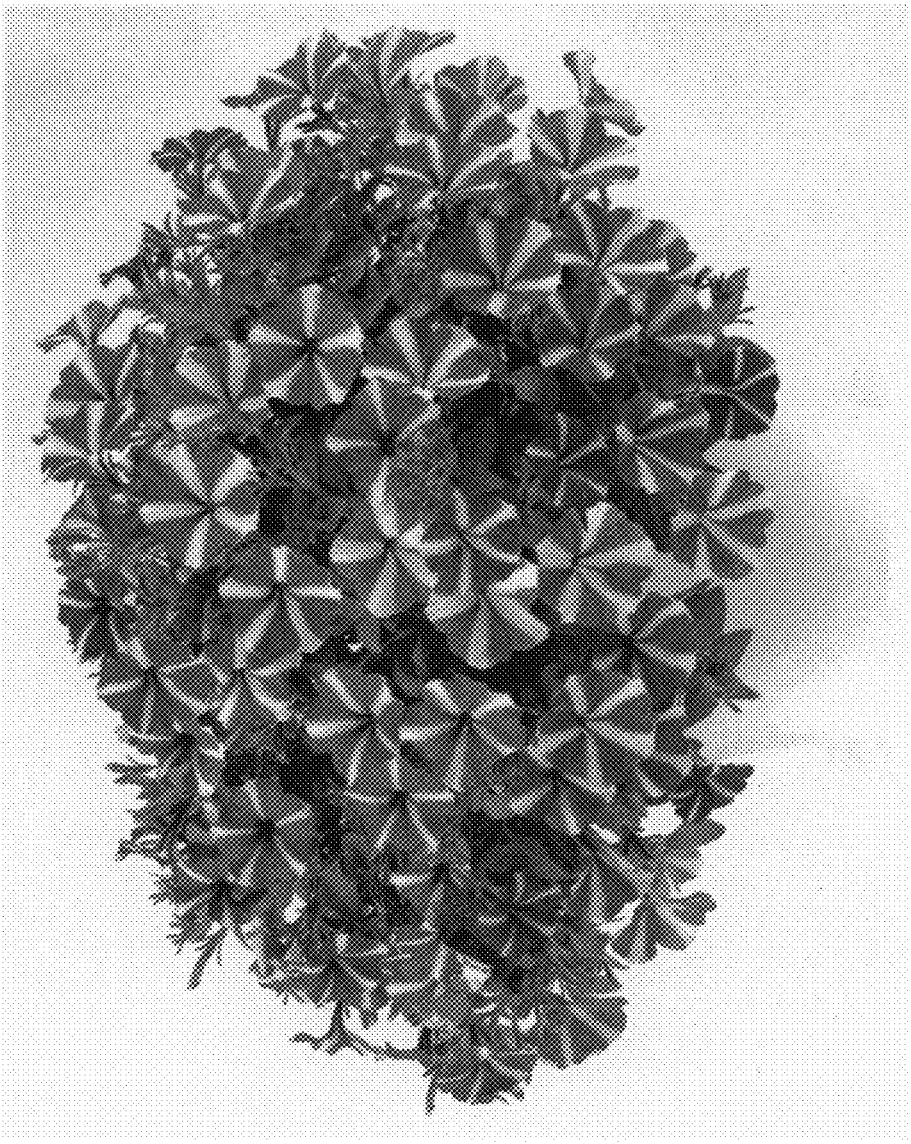

Latin name of the genus and species: *Petunia hybrida*.
Variety denomination: 'DAMORJOY'.

BACKGROUND OF THE INVENTION

The new *Petunia hybrida* cultivar is a product of a planned breeding program conducted by the inventor, Gavriel Danziger in Moshav Mishmar Hashiva, Israel. The objective of the breeding program was to produce new *Petunia* varieties with novel flower color patterns and large flowers. The cross resulting in this new variety was made during November of 2013.

The seed parent is the unpatented, propriety variety referred to as *Petunia* 'cv. 12-6189'. The pollen parent is the unpatented, propriety variety referred to as *Petunia* 'cv. 12-6657'. The new variety was discovered in July of 2014 by the inventor in a group of seedlings resulting from the 2013 crossing, in a research greenhouse in Moshav Mishmar Hashiva, Israel.

Asexual reproduction of the new cultivar 'DAMORJOY' was first performed by terminal vegetative cuttings during July of 2014, at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DAMORJOY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DAMORJOY' These characteristics in combination distinguish 'DAMORJOY' as a new and distinct *Petunia* cultivar:

1. Mounded growth habit.
2. Very well-branched plants with medium vigor.

3. Flowers color is burgundy purple with white stripes.
4. Large flower size.
5. Abundant flowering.

PARENT COMPARISON

Plants of the new cultivar 'DAMORJOY' are similar to plants of the seed parent, *Petunia* 'cv. 12-6189' in most horticultural characteristics, however, plants of the new cultivar 'DAMORJOY' differ in the following;

1. The seed parent has a trailing growth habit, the new variety is mounded.
2. The new variety produces many more branches per plant.
3. Flower color of the seed parent is white with purple stripes, flowers of the new variety are burgundy purple with white stripes.
4. Flowers of the new variety are larger than those of the seed parent.
5. The new variety flowers more abundantly.

Plants of the new cultivar 'DAMORJOY' are similar to plants of the pollen parent, *Petunia* 'cv. 12-6657' in most horticultural characteristics however, plants of the new cultivar 'DAMORJOY' differ in the following;

1. The pollen parent has a semi upright growth habit, the new variety is mounded.
2. Plants of the pollen parent are more vigorous, with slightly less branching than the new variety.
3. Flower color of the pollen parent is magenta with white stripes, the new variety is burgundy purple with white stripes.
4. Flower size of the pollen parent is larger than the new variety.
5. The new variety flowers more abundantly than the pollen parent.

COMMERCIAL COMPARISON

Plants of the new cultivar 'DAMORJOY' can be compared to the unpatented commercial variety *Petunia* hybrid 'Cascadias Bicolor Cabernet'. These varieties are similar in most horticultural characteristics; however, 'DAMORJOY' differs in the following:

1. Flower size of this comparator is smaller than the flower of the new variety.
2. Flower shape of the comparator is rounded, while the flower of the new variety is more star-shaped.
3. Plant habit of the comparator is semi-trailing, the new variety has a mounded growth habit.

Plants of the new cultivar 'DAMORJOY' can also be compared to the patented commercial variety *Petunia hybrida* 'DRAY67', U.S. Plant Pat. No. 25,906. These varieties are similar in most horticultural characteristics; however, 'DAMORJOY' differs in the following:

1. Flower size of the comparator is smaller than the flower size of the new variety.
2. Flower color of the comparator is black with yellow stripes, while the new variety has burgundy purple flowers with white stripes.
3. The comparator plant is taller than the new variety.

BRIEF DESCRIPTION OF THE PHOTOGRAPHS

The accompanying photograph in FIG. 1 illustrates in full color a typical plant of 'DAMORJOY' grown in a greenhouse, in Moshav Mishmar Hashiva, Israel.

Figure 2:
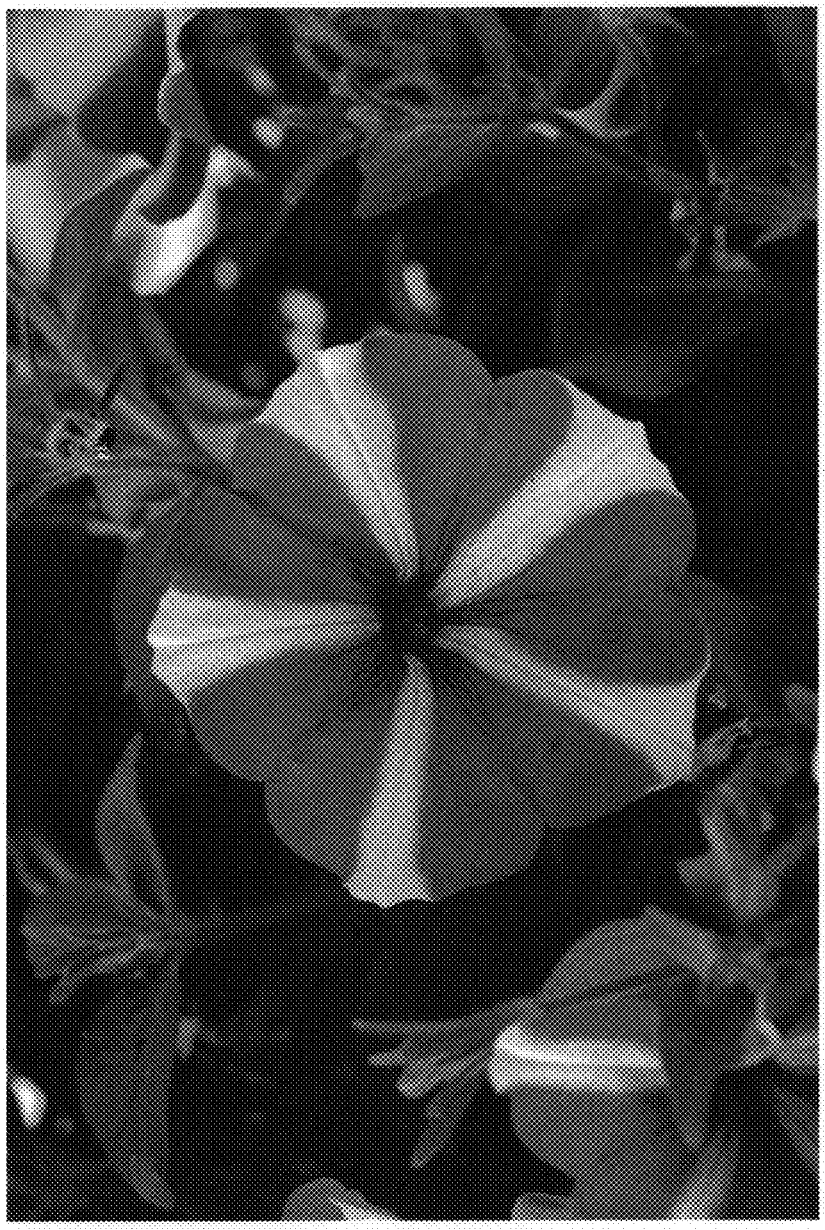

FIG. 2 illustrates in full color a typical mature flower of 'DAMORJOY' during Spring. Age of the plant photographed is approximately 90 days from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DAMORJOY' plants grown in greenhouse in Moshav Mishmar Hashiva, Israel, under natural lighting. Measurements were taken during April of 2015. The plants were approximately 90 days from a rooted cutting in a 13 cm pot. The growing temperature ranged from 20° C. to 35° C. during the days, 17° C. to 23° C. during the nights. Measurements and numerical values represent averages of typical plant types.

Botanical classification: *Petunia hybrida* 'DAMORJOY'.

PROPAGATION

Time to initiate roots: 10-14 days at approximately 20° C.
Root description: Fibrous. Colored tan and white, not accurately measured with R.H.S. chart.

PLANT

Growth habit: Mounded.
Pot size of plant described: 13 cm.
Height: To top of flowers: about 25 cm.
Plant spread: About 50 cm.
Growth rate: Medium.
Branching characteristics: Very well branched.
Length of primary lateral branches: About 25 cm.
Diameter of lateral branches: About 0.4 cm.
Quantity of primary lateral branches: 8.
Characteristics of primary lateral branches:
*Form*.—Cylindrical.
*Diameter*.—About 0.3 to 0.4 cm.
*Color*.—RHS Yellow-Green 146 C.
*Texture*.—Pubescent.
*Strength*.—Good.
Internode length: About 2 cm.

FOLIAGE

Leaf:
*Arrangement*.—Opposite.
*Quantity*.—Approximately 26 per branch.
*Average length*.—6.0 cm.
*Average width*.—3.0 cm.
*Shape of blade*.—Ovate.
*Apex*.—Acute.
*Base*.—Acute.
*Margin*.—Entire.
*Texture of top surface*.—Velvety.
*Texture of bottom surface*.—Velvety.
*Aspect*.—90 degrees.
*Color*.—Young foliage upper side: RHS Green N137 B. Young foliage under side: RHS Green N137 C. Mature foliage upper side: RHS Yellow-Green 146 A. Mature foliage under side: RHS Yellow-Green 146 B.
*Venation*.—Type: Pinnate. Venation color upper side: RHS Yellow-Green 146 C. Venation color under side: RHS Yellow-Green 146 D.
*Petiole*.—Length: About 1 cm. Diameter: About 0.4 cm. Color: RHS Yellow-Green 146 C.
*Texture*.—Velvety.

FLOWER

Natural flowering season: Spring, Summer and Autumn in Beit Dagan, Israel.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3 to 6 days.
Approximate quantity of flowers per plant: About 60.
Persistent or self-cleaning: Self-cleaning.
Bud:
*Shape*.—Tubular.
*Length*.—About 5 cm.
*Diameter*.—About 1 cm.
*Color*.—RHS Yellow-green 150 C with stripes Red-Purple 59 A.
Flower size:
*Diameter*.—About 6.5 cm.
*Flower tube length*.—About 3 cm.
*Flower tube diameter at distal end*.—1.2 cm.
*Flower tube diameter at proximal end*.—0.3 cm.
Petals:
*Length from throat*.—About 3 cm.
*Width*.—About 2.8 cm.
*Quantity*.—5.
*Texture*.—Velvety.
*Apex*.—Blunt.
*Margin*.—Slightly wavy, entire.

Color:

*When opening*.—Upper surface: RHS Red-Purple N79 B with 5 stripes, Red-Purple 71 A. Lower surface: RHS Red-Purple N79 D with 5 stripes, Yellow-Green 150 D.

*Fully opened*.—Upper surface: RHS Red-Purple 71 A with 5 stripes, White N155 C. Lower surface: RHS Red-Purple 71 B with 5 stripes, White N155 C. Flower throat (inside): RHS Yellow-Green 150 D with Veins, Yellow-Green 150A and 5 stripes Red-Purple 71 A with veins Purple 79B. Flower throat, vein: RHS Purple 79 B. Flower tube (outside): RHS Yellow-Green 150 D with 5 stripes, Purple 79 B. Flower tube, vein: RHS Yellow-Green 150 A.

*Fading*.—Petals fading to: RHS Purple N78 A with 5 stripes, White N155 C.

Calyx/sepals:

*Quantity per flower*.—5.

*Shape*.—Linear.

*Length*.—About 2.0 cm.

*Width*.—About 0.3 cm.

*Apex*.—Rounded.

*Base*.—Cuneate.

*Margin*.—Entire.

*Texture*.—Velvety.

*Color*.—Upper Surface: RHS Green 137 B. Lower Surface: RHS Green 137 C.

Pedicel:

*Length*.—About 2.7 cm.

*Diameter*.—About 0.2 cm.

*Color*.—RHS Green 137 C.

*Orientation*.—45 degrees.

Peduncle: Not present.

Pedicel:

*Length*.—About 2.0 cm.

*Diameter*.—About 0.2 cm.

*Color*.—RHS Yellow-Green 146 B.

*Orientation*.—45 degrees.

Fragrance: None.

REPRODUCTIVE ORGANS

Stamens:

*Number*.—5.

*Filament length*.—About 2.2 cm.

Anthers:

*Length*.—About 0.2 cm.

*Shape*.—Rounded.

*Color*.—RHS Violet-Blue 95 D.

*Pollen*.—Color: RHS Blue 106 C. Quantity: Abundant.

Pistil:

*Number*.—1.

*Length*.—About 2.7 cm.

*Style*.—Length: About 2 cm. Color: RHS Yellow-Green 145 C.

*Stigma*.—Shape: Rounded. Color: RHS Yellow-Green 144 B. Ovary Color: RHS Yellow-Green 143 A.

OTHER CHARACTERISTICS

Seeds and fruits: About 80 Brown, rounded seeds of about 0.5 mm diameter, per one brown, conical capsule.

Disease/pest resistance: Neither resistance nor susceptibility to the normal diseases and pests of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DAMORJOY' as herein illustrated and described.

* * * * *